US005549580A

United States Patent [19]

Diaz

[11] Patent Number: 5,549,580
[45] Date of Patent: Aug. 27, 1996

[54] CATHETER HAVING A FLEXIBLE DISTAL TIP AND METHOD OF MANUFACTURING

[75] Inventor: Juan C. Diaz, Miami, Fla.

[73] Assignee: Cordis Corporation, Miami Lakes, Fla.

[21] Appl. No.: 376,842

[22] Filed: Jan. 23, 1995

[51] Int. Cl.⁶ ............................................. A61M 25/00
[52] U.S. Cl. ....................... 604/280; 604/96; 606/194; 128/772
[58] Field of Search ........................... 604/282, 280, 604/96, 281, 264; 606/191, 192, 194; 128/772, 656, 657, 658

[56] References Cited

U.S. PATENT DOCUMENTS

| | | | |
|---|---|---|---|
| Re. 33,166 | 2/1990 | Samson | 606/194 |
| 3,973,556 | 8/1976 | Fleischhacker et al. | |
| 4,577,637 | 3/1986 | Mueller, Jr. | 128/658 |
| 4,669,465 | 6/1987 | Moore et al. | |
| 4,676,249 | 6/1987 | Arenas et al. | 128/657 |
| 4,715,378 | 12/1987 | Pope, Jr. et al. | 606/194 |
| 4,771,778 | 9/1988 | Mar | |
| 4,784,636 | 11/1988 | Rydell | 604/22 |
| 4,846,186 | 7/1989 | Box et al. | 128/657 |
| 4,955,862 | 9/1990 | Sepetka | 604/164 |
| 5,002,559 | 3/1991 | Tower | 128/772 |
| 5,095,915 | 3/1992 | Engelson | 128/772 |
| 5,102,403 | 4/1992 | Alt | 604/280 |
| 5,108,407 | 4/1992 | Geremia et al. | 606/108 |
| 5,120,323 | 6/1992 | Shockey et al. | 604/282 |
| 5,129,890 | 7/1992 | Bates et al. | 128/657 |
| 5,156,595 | 10/1992 | Adams | 604/96 |
| 5,226,421 | 7/1993 | Frisbie et al. | 128/772 |
| 5,242,394 | 9/1993 | Tremulis | 128/657 |
| 5,269,793 | 12/1993 | Simpson | 606/159 |
| 5,279,561 | 1/1994 | Roucher et al. | 604/96 |
| 5,300,025 | 4/1994 | Wantink | 604/96 |
| 5,312,340 | 5/1994 | Keith | 604/96 |
| 5,318,529 | 6/1994 | Kontos | 604/96 |
| 5,318,587 | 6/1994 | Davey | 606/194 |
| 5,387,225 | 2/1995 | Euteneuer et al. | 604/96 |
| 5,409,470 | 4/1995 | McIntyre et al. | 604/280 |
| 5,423,771 | 6/1995 | Imran | 604/96 |
| 5,441,484 | 8/1995 | Atkinson et al. | 604/96 |
| 5,443,907 | 8/1995 | Slaikeu et al. | 128/657 |

FOREIGN PATENT DOCUMENTS 9323107  11/1993  WIPO ............................ 604/282

OTHER PUBLICATIONS

Cordis Brochure, "Discover the Benefits of a Sleek Physique", 1993.

Primary Examiner—John D. Yasko
Assistant Examiner—Ronald K. Stright, Jr.
Attorney, Agent, or Firm—Allen, Dyer, Doppelt, Eranjola & Milbrath, P.A.

[57] ABSTRACT

A catheter includes an elongate body defining a core wire having a projection extending radially outwardly adjacent a distal end. The projection may be an enlarged diameter portion of the core wire integrally formed with the core wire. A coil spring covers the distal end and has a proximal end engaging the projection. A tube, such as a tubular portion or leg of a balloon, has a distal end fusibly sealed to the proximal end of the coil spring. Because the coil spring is mechanically secured to the core wire, no solder is needed. In addition, the distal end of the tube further includes heat fused portions thereof filling interstices between adjacent coils of the coil spring and the core wire. The distal end of the tube is fusibly sealed to the coil spring so that adjacent coils of the coil spring are movable relative to one another to define a flexible tip portion for the catheter having substantially uniform flexibility. A method for making the catheter is also disclosed.

25 Claims, 3 Drawing Sheets

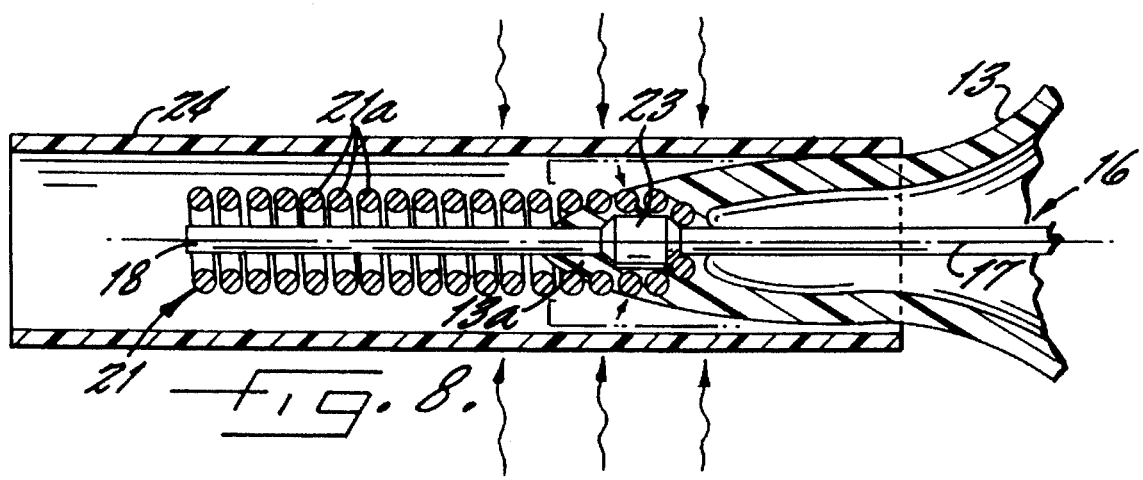
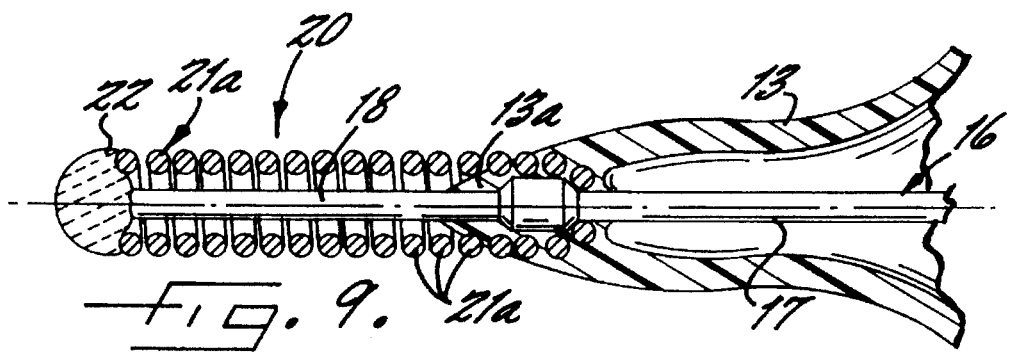

CATHETER HAVING A FLEXIBLE DISTAL TIP AND METHOD OF MANUFACTURING

FIELD OF THE INVENTION

The present invention relates to the field of intravascular catheters and, more particularly, relates to an intravascular dilatation catheter and associated fabrication method.

BACKGROUND OF THE INVENTION

Intravascular catheters are used in a variety of therapeutic and diagnostic techniques. For example, in angioplasty procedures to treat stenotic arteriosclerotic disease, a catheter having an expandable section, such as a balloon at the distal end, is inserted into and guided through the vascular system. When the balloon is positioned adjacent the stenotic lesion to be treated, the balloon is inflated to compress the stenotic plaque against the blood vessel wall, thereby improving blood flow through the artery. Angioplasty is widely used for reducing stenotic lesions in the coronary arteries, although stenoses in other parts of the vascular system may also be treated.

Other types of intravascular catheters are also known that include a rotatable cutter at the distal tip which, when activated, excises obstructive lesions (see, e.g., U.S. Pat. No. 4,784,636). Catheters incorporating fiberoptic bundles to remove arterial plaques via directed laser light are also known (see, e.g., U.S. Pat. No. 4,669,465).

Catheters which are directly involved in improving blood flow through an artery (whether by expansion, excision or ablation) are typically termed "working catheters." To position a working catheter near the treatment site within the blood vessel, a guide catheter which is distinct from the working catheter may be used. Typical guide catheters comprise an elongated flexible tube having an internal lumen sufficiently large to receive and pass the working catheter therethrough.

Angioplasty, for example, is commonly performed using a working catheter which has an inflatable balloon at its distal end and commonly referred to as a dilatation or balloon catheter. During insertion the balloon is typically deflated and once positioned the balloon is inflated, for example, by filling with fluid under pressure.

Dilatation catheters typically include over-the-wire and on-the-wire type catheters. An over-the-wire catheter contains an inflation lumen by which the balloon is inflated when positioned, and a separate guide wire lumen through which a guide wire is advanced into the vasculature. The dilatation catheter is advanced by alternately advancing the distal end of the guide wire, then advancing the catheter over the guide wire.

In contrast to an over-the-wire catheter, one type of on-the-wire dilatation catheter contains a core wire which is integral with the dilatation balloon. In such a catheter, the core wire, balloon and inflation lumen form a single unit. Typically a flexible distal tip made of helically coiled wire is provided at the distal end of the core wire. The flexible distal tip may be bent at a predetermined angle to facilitate steering of the core wire to a desired blood vessel at a branch point by selectively rotating a proximal end of the core wire while viewing the distal tip by fluoroscopy.

U.S. Pat. No. 5,312,340 to Keith entitled Balloon Dilatation Catheter Having Dual Sealing Plugs discloses a catheter in which a sealing plug extending annularly about the core wire separates the distal end of the balloon member from the flexible coil tip. The flexible coil tip is attached to the core wire by solder or braze. In one disclosed embodiment, the distal end of the balloon extends over the proximal portion of the flexible coil tip, which is soldered or brazed to the core wire. The balloon material is not joined or sealed to the flexible coil tip, allowing the balloon to rotate about the flexible coil tip and the core wire.

In a typical on-the-wire balloon catheter, the distal end or leg of the balloon is connected to the core wire, and the flexible tip is secured to a portion of the core wire which extends distally beyond the balloon. For example, U.S. Pat. No. 4,771,778 to Mar entitled Steerable Low Profile Balloon Dilatation Catheter discloses a balloon catheter having the distal end of the balloon secured to the core wire using means such as an adhesive, and a flexible coil spring tip secured to the core wire by means such as solder. Similarly, U.S. Pat. No. 5,156,595 to Adams entitled Dilatation Balloon Catheter and Method of Manufacture discloses an on-the-wire balloon catheter having a core wire with a flexible coil spring extending distally therefrom. The distal balloon end is attached to the core wire using an adhesive such as epoxy; and the flexible coil spring is secured to the core wire using a braze or solder connection.

U.S. Pat. No. Re. 33,166 to Samson entitled Steerable Dilatation Catheter discloses a dilatation catheter wherein the balloon is secured to the core wire by adhesive, and the flexible helical coil is connected to the core wire by epoxy. A filler, such as epoxy, is used to define a smooth transition region between the distal end of the balloon and the proximal end of the flexible helical coil. The patent further discloses that means other than adhesives can be used to secure the balloon to the core wire, such as direct fusion or the use of a clamp.

In other types of on-the-wire catheters, solder is commonly used to connect the proximal end of the coil spring to the core wire. The distal portion or leg of the balloon is positioned over the soldered area and reheated to cause the thermoplastic balloon material to melt and fuse onto the coil spring and core wire. Unfortunately, solder may reflow distally along the core wire when the balloon is heated. The reflowed solder wicks forward along adjacent coils of the coil spring toward the distal end thereof. The reflowed solder, once cooled, results in an area of increased stiffness along the distal tip adjacent the distal end of the balloon. Accordingly, the distal tip is no longer flexible along its entire length as is desirable to facilitate bending and steering of the core wire through the vascular system.

SUMMARY OF THE INVENTION

In view of the foregoing it is therefore an object of the present invention to provide a catheter and an associated fabrication method so that the catheter retains flexibility throughout its distal tip portion.

This and other objects, advantages and features of the present invention are provided by a catheter including an elongate body defining a core wire having a projection extending generally radially outwardly adjacent a distal end; a coil spring covering the distal end of the core wire and having a proximal end engaging the projection; and a tube having a distal end being fusibly sealed to the proximal end of the coil spring. The tube is preferably the tubular shaped leg or distal end portion of a balloon surrounding the core wire. Because the coil spring is mechanically secured to the core wire, solder is not needed. In addition, the distal end of the tube further includes heat fused portions thereof filling interstices between adjacent coils of the coil spring and the core wire thereby encapsulating the mechanical connection between the coil spring and core wire.

According to one advantage of the invention, when the distal end of the tube is fusibly sealed to the coil spring, there is no solder to reflow and reduce the flexibility of the coils adjacent the distal end of the tube. Rather, the adjacent coils of the coil spring are movable relative to one another to define a flexible tip portion for the catheter having substantially uniform flexibility.

The projection on the core wire is preferably generally annularly shaped and is integrally formed with the core wire. Stated in different terms, the projection is preferably provided by an enlarged diameter portion of the core wire, such as may be formed by precision centerless grinding. Proximal coils of the coil spring may be deformed radially inwardly or crimped adjacent a proximal side of the enlarged diameter portion to secure the spring by an interference fit.

A method according to the present invention is for making a catheter as described above. The method preferably includes the steps of: forming a generally radially outwardly extending projection adjacent a distal end of an elongate body defining a core wire; positioning a coil spring over the distal end of the core wire and securing a proximal end of the coil spring to the core wire at the projection; positioning a distal end of a tube over the proximal end of the coil spring, the tube comprising heat fusible material; and heating the distal end of the tube to fusibly seal the distal end onto the proximal end of the coil spring. The step of heating the distal end of the tube preferably further includes heating same to fuse portions of the distal end to fill interstices between adjacent coils of the coil spring and the core wire.

The step of forming the projection preferably comprises integrally forming an enlarged diameter portion of the core wire, such as by precision centerless grinding. The step of securing the proximal end of the coil spring preferably comprises radially inwardly deforming portions of the coil spring adjacent a proximal side of the projection. The step of heating the distal end of the tube preferably leaves exposed adjacent coils of the coil spring movable relative to one another to define a flexible tip portion for the catheter.

BRIEF DESCRIPTION OF THE DRAWINGS

FIG. 8 is a cross-sectional view of the core wire, coil spring, and balloon leg and illustrating heating and fusing of the balloon leg onto the coil spring according to the method of the invention.

FIG. 9 is a cross-sectional view of the core wire, coil spring, and balloon leg illustrating the catheter as completed according to the method of the invention.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Figure 1:
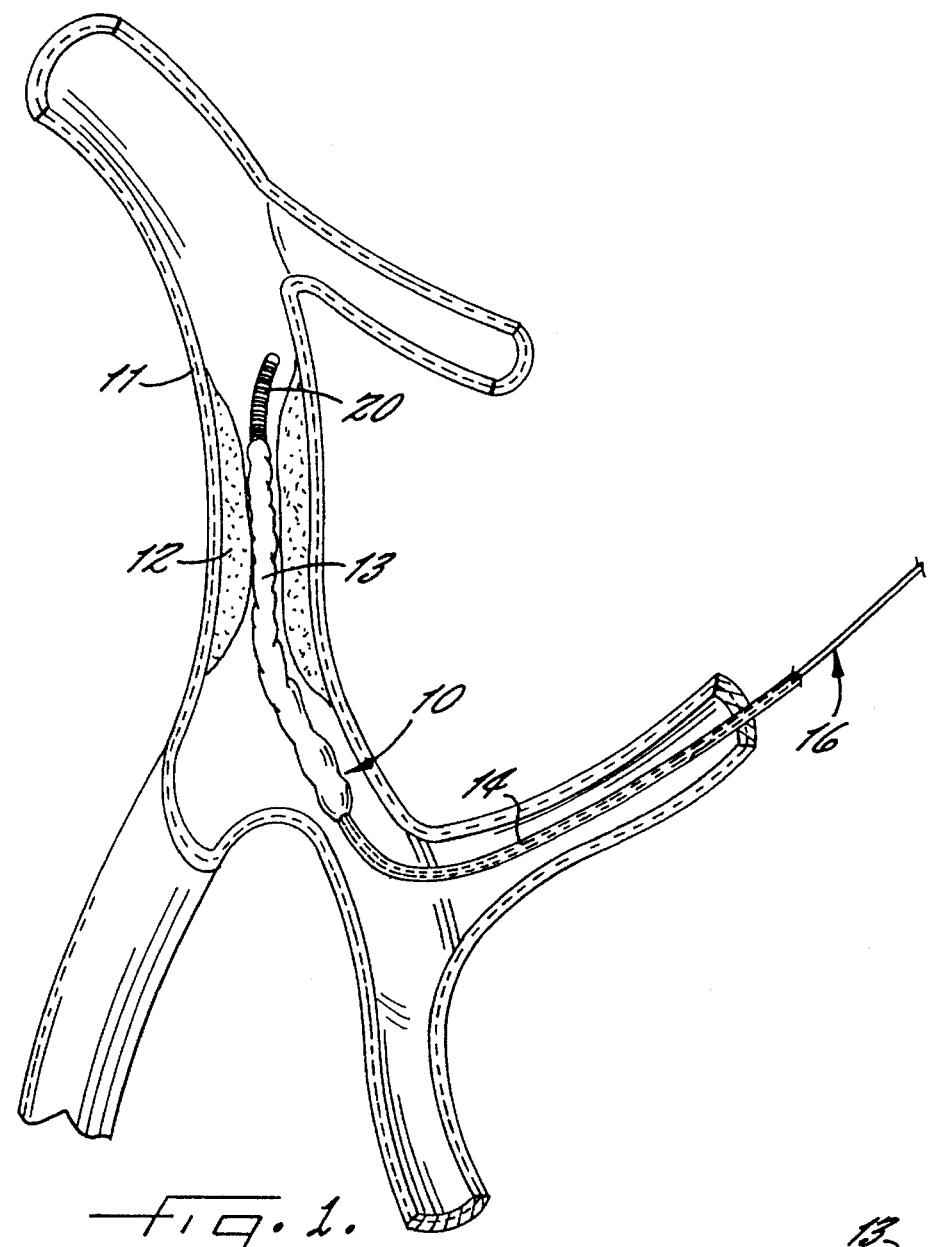
FIG. 1 is a schematic fragmentary view of the catheter according to the invention positioned within a blood vessel.
Figure 2:
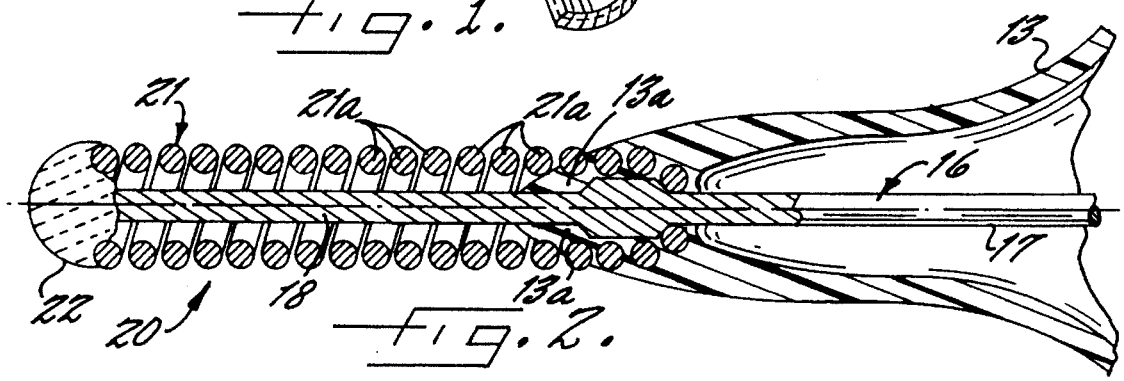
FIG. 2 is a greatly enlarged cross-sectional view of a distal end portion of the catheter as shown in FIG. 1.

Referring now to FIGS. 1 & 2, a balloon catheter 10 according to the invention is shown inserted into an occluded blood vessel 11 containing an obstruction 12. The catheter 10 according to the invention includes a balloon 13 which may be inflated through an adjacent tubular section 14 to compress the obstruction 12 thereby increasing blood flow through the vessel 11.

The catheter 10 comprises a core wire 16 preferably formed of an elongate flexible unitary body having a longitudinally extending main section 17 and a distal tip section 18. The total length of the core wire 16 is determined by the use for which it is intended, for example, preferably about 65 inches for an angioplasty balloon catheter 10 as illustrated. The core wire 16 is preferably a wire formed of a material such as stainless steel, nickel, titanium or alloys of nickel, as would be readily understood by those skilled in the art, and may be radiopaque to facilitate imaging. A radiopaque marker band, not shown, may be positioned on the core wire 16 underlying the balloon 13 as would be readily understood by those skilled in the art. The core wire 16 typically has a circular cross-sectional shape of predetermined diameter, although other cross-sectional shapes may be used as would be understood by one skilled in the art.

A projection, such as illustratively provided by an enlarged diameter portion 23, extends generally radially outwardly from the core wire 16 intermediate the distal tip section 18 and the main section 17. The enlarged diameter portion 23 is preferably generally annularly shaped and integrally formed with the core wire, such as by precision centerless grinding as would be appreciated by those skilled in the art. For a typical catheter 10, the enlarged diameter portion 23 may have a diameter of about 0.0055 inches, while the adjacent portions of the core wire are about 0.0025 inches in diameter. In addition, the length of the enlarged diameter portion 23 may be about 0.025 inches.

The flexible tip 20 may be provided by a wound coil spring 21 comprising a plurality of spirally wound coils 21a covering the distal tip section 18 of core wire 16. The flexible tip 20 is bendable and shape-retaining to permit the setting of a predetermined angle or curvature in the flexible tip to enhance steerability within the vascular system. The proximal end of the coil spring 21 engages the enlarged diameter portion 23 of the core wire 16 to thereby secure the coil spring to the core wire by an interference fit. More particularly, the coil spring 21 is secured by crimping or deforming coils radially inwardly adjacent the proximal side of the enlarged diameter portion 23. Stated another way, the coil spring 21 is mechanically secured to the core wire by an interference fit at a position proximal to the projection provided by the enlarged diameter portion 23. Because the coil spring 21 is mechanically secured to the core wire 16, no solder is needed to secure the coil spring to the core wire.

A tube comprising heat fusible material, such as the leg of the balloon 13, is fusibly sealed to the proximal end of the coil spring 21. As would be readily understood by those skilled in the art, the tube may be nylon or another thermoplastic material. Preferably heat fusible material of the tube fills the interstices 13a between adjacent coils 21a of the coil spring 21 and the core wire 16 to secure the balloon 13, as well as seal the balloon to the core wire. The distal tip 22 of the coil spring may be welded, soldered, brazed or otherwise formed into a generally hemispherical shape as illustrated. A smooth distal tip 22 facilitates passage of the catheter 10 through the vasculature, as would be readily understood by those skilled in the art.

The provision of the coil spring 21 mechanically secured to the core wire 16, and the tube balloon leg 13 fusibly sealed to the proximal end of coil spring 21 provides a flexible tip 20 having substantially uniform flexibility from the distal end of the tube 13 to the distal end of the tip. Stated in other terms, the adjacent coils 21a are free to move relative to one another, in sharp contrast to conventional catheters wherein reflowed solder reduces flexibility of the tip.

Figure 3:
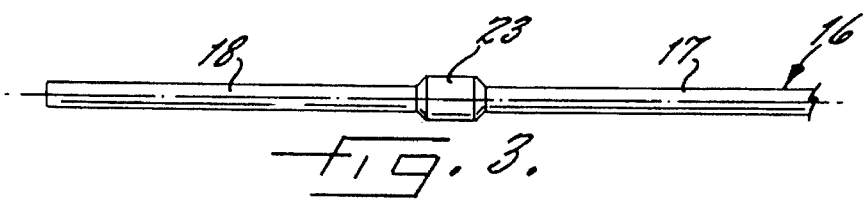
FIG. 3 is a side elevational view of the core wire of the catheter according to the invention.

A method aspect of the present invention is for forming the catheter 10 as described above, and is explained with further reference to FIGS. 3–9. The method includes the step of forming a core wire 16 having a main section 17 and a distal tip section 18, with a projection therebetween as shown in FIG. 3. The forming of the projection on the core wire 16 is preferably carried out by forming an enlarged diameter portion 23 of the core wire 16 (FIG. 3) such as by the process of precision centerless grinding available as a service from Microguide Co. of Tehachare, Calif.

Figure 4:
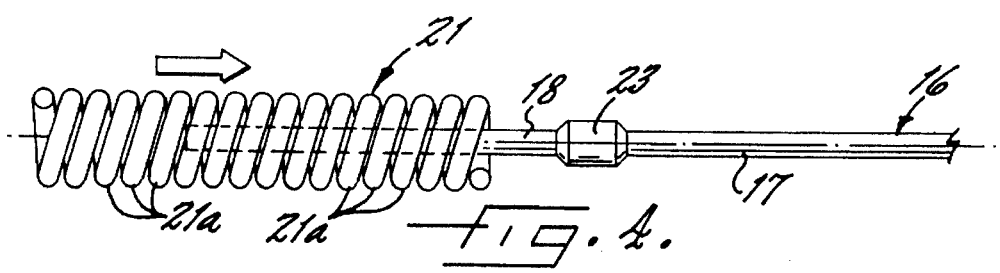
FIG. 4 is a side elevational view of the core wire and coil spring illustrating positioning of the coil spring on the core wire according to the method of the invention.
Figure 5:
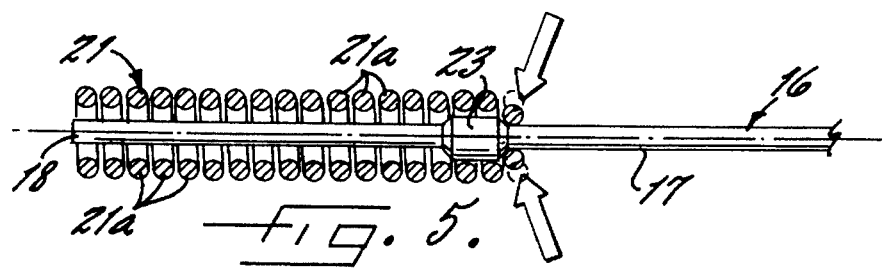
FIG. 5 is a cross-sectional view of the core wire and coil spring illustrating crimping of the coil spring onto the core wire according to the method of the invention.
Figure 6:
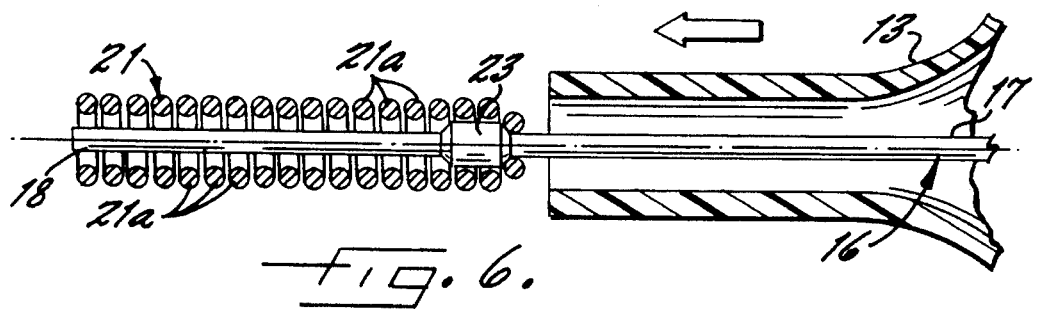
FIG. 6 is a cross-sectional view of the core wire, coil spring, and tube provided by the balloon leg and illustrating positioning of the balloon leg over the coil spring according to the method of the invention.

As shown in FIGS. 4 & 5, a coil spring 21 is positioned over the distal end of the core wire 16 and secured at a proximal end to the core wire at the projection or enlarged diameter portion 23. Preferably the step of securing the proximal end of the coil spring 21 to the core wire 16 is performed by radially inwardly deforming or crimping portions of the coil spring adjacent a proximal side of the projection, as shown in FIG. 5.

The distal end of the tube defined by the balloon 13 is positioned over the proximal end of the coil spring 21 (FIG. 6), and the distal end of the balloon 13 is heated (FIGS. 7 & 8) to fusibly seal the distal end onto the proximal end of the coil spring 21. More particularly, the method includes the step of securing the distal end of balloon 13 over the proximal end of coil spring 16 without reducing the flexibility of the exposed distally extending portion of the coil spring 21. Preferably, this is carried out by positioning the balloon 13 over the proximal end of the coil spring 16 (FIG. 6) and heating the distal end of the balloon leg, such that the interstices 13a between adjacent coils 21a of the coil spring 21 and the core wire are filled with the heat fused material. Accordingly, adjacent coils 21a of the coil spring 21 remain movable relative to one another to define a flexible tip 20 for the catheter 10.

Figure 7:
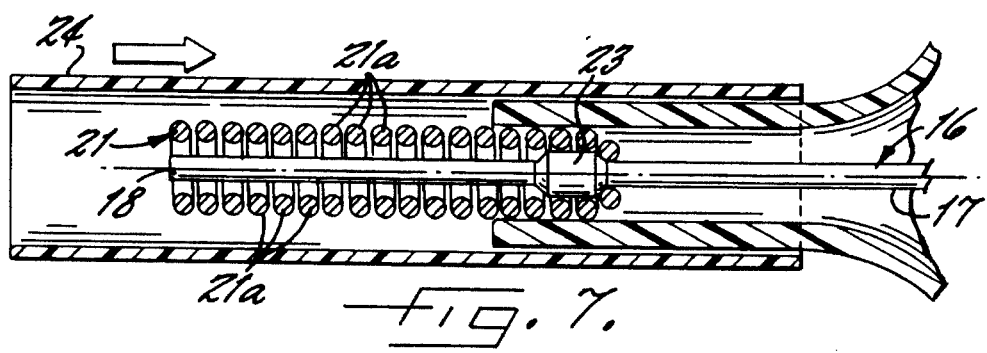
FIG. 7 is a cross-sectional view of the core wire, coil spring, and balloon leg and illustrating positioning of a heating sleeve over the balloon leg according to the method of the invention.

The step of heating the distal end of tube or balloon 13 to fusibly seal it to coil spring 21 may be accomplished by a variety of methods as would be appreciated by those skilled in the art. As illustrated in FIGS. 7 & 8, a Teflon heating sleeve 24 may be positioned over the distal end of the balloon 13 to transfer heat to the distal end of the balloon leg to thereby fusibly seal it to the coil spring 21, while also encapsulating the mechanical connection of the coil spring and enlarged diameter portion 23. The Teflon heating sleeve 24 may then be readily removed. The distal tip 22 of the coil spring 21 may be shaped by conventional methods to provide a rounded over or hemispherical surface. Exemplary methods include soldering or brazing to achieve the desired tip 22 shape.

In the drawings and specification, there have been disclosed typical preferred embodiments of the invention and, although specific terms are employed, they are used in a generic and descriptive sense only and not for purposes of limitation, the scope of the invention being set forth in the following claims.

That which is claimed is:

1. A catheter comprising:

an elongate body defining a core wire;

a projection extending generally radially outwardly from said core wire adjacent a distal end thereof;

a coil spring covering the distal end of said core wire, said coil spring having a proximal end engaging said projection to secure the coil spring to said core wire; and a tube having a lumen and a distal end surrounding the proximal end of said coil spring, the distal end of said tube comprising heat fusible material being fusibly sealed to the proximal end of said coil spring and adjacent portions of the core wire to form a fluid seal for said lumen.

2. A catheter according to claim 1 said coil spring comprises a plurality of coils spirally wound about the distal end of said core wire.

3. A catheter according to claim 2 wherein adjacent coils of said coil spring are movable relative to one another to define a flexible tip portion for the catheter.

4. A catheter according to claim 3 wherein said coil spring has substantially uniform flexibility from the distal end of said tube to the distal end of said coil spring.

5. A catheter according to claim 2 wherein the distal end of said tube further comprises heat fused portions filling interstices between adjacent coils of said coil spring and said core wire.

6. A catheter according to claim 1 wherein said projection is generally annularly shaped and is integrally formed with said core wire.

7. A catheter according to claim 1 wherein the proximal end of said coil spring is deformed radially inwardly adjacent a proximal side of said projection.

8. A catheter according to claim 1 wherein said tube comprises a balloon surrounding said core wire.

9. A catheter according to claim 1 wherein said coil spring comprises a radiopaque material.

10. A catheter comprising:

an elongate body defining a core wire and having an enlarged diameter portion adjacent a distal end thereof;

a coil spring covering the distal end of said core wire, said coil spring having a proximal end surrounding and engaging said enlarged diameter portion of said core wire so as to form an interference fit therewith; and a tube having a lumen surrounding said core wire and having a distal end secured to the proximal end of said coil spring to form a fluid seal at said distal end.

11. A catheter according to claim 10 wherein said coil spring comprises a plurality of coils spirally wound about the distal end of said core wire.

12. A catheter according to claim 11 wherein said tube comprises heat fusible material, and wherein the distal end of said tube is fusibly sealed to the proximal end of said coil spring so as to fill interstices between adjacent coils of said coil spring and said core wire.

13. A catheter according to claim 12 wherein adjacent coils of said coil spring are movable relative to one another to define a flexible tip portion for the catheter.

14. A catheter according to claim 10 wherein said tube comprises heat fusible material, and wherein the distal end of said tube is fusibly sealed to the proximal end of said coil spring.

15. A catheter according to claim 10 wherein said coil spring has substantially uniform flexibility from the distal end of said tube to the distal end of said coil spring.

16. A catheter according to claim 10 wherein the proximal end of said coil spring is deformed radially inwardly adjacent a proximal side of the enlarged diameter portion of said core wire.

17. A catheter according to claim 10 wherein said tube comprises a balloon surrounding said core wire.

18. A catheter according to claim 10 wherein said coil spring comprises a radiopaque material.

19. A catheter comprising:

an elongate body defining a core wire;

a projection integrally formed with said core wire and extending generally radially outwardly from said core wire adjacent a distal end thereof;

a coil spring covering the distal end of said core wire, said coil spring having a proximal end engaging said projection so as to form an interference fit therewith; and a tube having a lumen and a distal end surrounding the proximal end of said coil spring, the distal end of said tube comprising heat fusible material being fusibly sealed to the proximal end of said coil spring to form a fluid seal for said lumen.

20. A catheter according to claim 19 wherein said coil spring comprises a plurality of coils spirally wound about the distal end of said core wire.

21. A catheter according to claim 20 wherein the heat fusible material of the distal end said tube further comprises portions filling interstices between adjacent coils of said coil spring and said core wire.

22. A catheter according to claim 19 wherein said coil spring has substantially uniform flexibility from the distal end of said tube to the distal end of said coil spring.

23. A catheter according to claim 19 wherein said projection is generally annularly shaped.

24. A catheter according to claim 19 wherein the proximal end of said coil spring is deformed radially inwardly adjacent a proximal side of said projection.

25. A catheter according to claim 19 wherein said tube comprises a balloon surrounding said core wire.

* * * * *